US00PP10705P

United States Patent [19]

Tachibana

[11] Patent Number: Plant 10,705

[45] Date of Patent: Nov. 24, 1998

[54] VERBENA PLANT NAMED 'SUNVP-PI'

[75] Inventor: Ryuichi Tachibana, Yamato, Japan

[73] Assignee: Suntory Limited, Osaka, Japan

[21] Appl. No.: 746,562

[22] Filed: Nov. 13, 1996

[51] Int. Cl.[6] ..... A01H 5/00

[52] U.S. Cl. ..... Plt./87

[58] Field of Search ..... Plt./87

[56] References Cited

U.S. PATENT DOCUMENTS

| | | | |
|---|---|---|---|
| P.P. 8,995 | 11/1994 | Tachibana et al. | Plt./87 |
| P.P. 9,014 | 12/1994 | Tachibana et al. | Plt./87 |
| P.P. 9,059 | 2/1995 | Tachibana et al. | Plt./87 |
| P.P. 9,085 | 3/1995 | Tachibana et al. | Plt./87 |
| P.P. 9,121 | 4/1995 | Tachibana et al. | Plt./87 |
| P.P. 9,411 | 12/1995 | Tachibana et al. | Plt./87 |

*Primary Examiner*—James R. Feyrer
*Assistant Examiner*—Elizabeth C. Kemmerer
*Attorney, Agent, or Firm*—Morgan & Finnegan; Eugene Moroz; Mary J. Morry

[57] ABSTRACT

Disclosed herein is a verbena plant has spread growth habit having long stems and spreading area of plant of broad. The plant has abundant branching and a plentiful number of flowers in a spike, and a great profusion of blooms. The Blooming period is late April to November and flowering duration is long. The whole bush remains in bloom for a considerable period of time. The flower size is large and the petal color of the flower is a deep purplish pink color. The plant has high tolerances to cold and heat, high resistance to pests and diseases, particularly powdery mildew, and high resistance to rain.

2 Drawing Sheets

BACKGROUND OF THE VARIETY

The present invention relates to a new and distinct variety of verbena plant obtained from a crossing "Derby Rosa" (♀) and a wild type of verbena plant *Verbena peruviana f. rosea.* (♂) native to Brazil.

The verbena is a very popular plant and is used for flower bedding and potting in the summer season. There are only a few varieties of the verbena plant which have a spread growth habit, much branching, many number of flowers in a spike and which have a high resistance to rain, heat, cold, and diseases. Accordingly, this invention was aimed at obtaining a new variety having a spread growth habit, strongly branching, many number of flowers in a spike, large diameter flower, high tolerance to heat and cold, and resistances to diseases and pests, and also having a is deep purplish pink color petal.

The new variety of verbena plant according to this invention originated from crossing of "Derby Rosa" (♀) and a wild type of verbena plant *Verbena peruviana f. rosea.* (♀) native to Brazil. First of all, 15 seedlings were obtained from crossing "Derby Rosa" as female parent and a wild type of verbena plant (*Verbena peruviana f. rosea*) as pollen parent in the spring of 1989. From this crossing 3 seedlings were selected in view of spread growth habit and propagated by cutting, and then grown as a trial by flower bedding and planter from in the spring of 1990. And then 2 seedlings which were selected from these 3 seedlings were carried out in a trial by flower potting and bedding from in the spring of 1991 and the botanical characteristics of 2 seedlings were then examined, using similar variety "Derby salmon rose" for comparison. Finally only one plant was selected. As a result, it was concluded that this verbena is distinguishable from any other variety, whose existence is known to us, sufficiently uniform and stable in its characteristics, then this new variety of verbena plant was named "Sunvp-Pi".

In the following description, the color-coding is in accordance with The Horticultural Color Chart of The Royal Horticultural Society, London, England (R.H.S. Colour Chart), and the Inter- Society color Council-Nation Bureau of Standard Color Name (I.S.C.C.-N.B.S. Color Name). A color chart based on The Japan Color Standard for Horticultural Plant (J.H.S. Color Chart) is also added for reference.

The "Derby Rosa" used as female parent in the obtaining of this new variety "Sunvp-Pi", is bred by the Bebary Corp., Germany and is on the market. The "Derby Rosa" series includes "Derby salmon rose", "Derby scarlet" and the like. The main botanical characteristics of "Derby Rosa" are as follows.

Plant:
- *Growth habit.*—Semi-erect.
- *Plant height.*—15–20 cm.
- *Plant extension.*—30–50 cm.

Stem:
- *Diameter.*—2.0–3.0 mm.
- *Anthocyanin pigmentation.*—Absent.
- *Branching.*—Medium.
- *Pubescence.*—Medium.
- *Length of internode.*—3.0–5.0 cm.

Leaf:
- *Phyllotaxis.*—Opposite.
- *Shape of blade.*—Oblong.
- *Length.*—3.0–4.0 cm.
- *Width.*—2.0–2.5 cm.
- *Depth of incison.*—None, no incision.
- *Color.*—Dark olive green (R.H.S. 137B, 147A, JHS 3707)
- *Pubescence.*—Medium.

Flower:
- *Facing direction.*—Upward.
- *Outward curvature of petal.*—None.
- *Diameter.*—1.5–2.0 cm.
- *Height.*—15–20 mm.
- *Color.*—Vivid red(R.H.S. 53D, JHS 0106).
- *Color intensity.*—Absent.
- *Overlapping of petals.*—Closed.
- *Spike.*—30–40 mm in length; and 50–60 mm in diameter.
- *Calyx.*—1.0–1.5 cm in length.
- *Anthocyanin pigmentation of calyx limb.*—Present.

*Peduncle*.—2–3 mm in thickness; and 5.0–6.0 cm in length.
*Number of flowers*.—Medium (10–13).
*Reproductive organs*.—1 pistil and 5 stamens.
*Flower fragrance*.—Absent.
*Flowering duration*.—Medium.
Physiological and ecological characteristics: Low resistance to diseases and pests, low tolerances to heat and cold.

The pollen parent used in the obtaining of this new variety "Sunvp-Pi" was a wild type of verbena native to South Brazil and *Verbena peruviana f. rosea*. This wild type of verbena plant is presently maintained at the Plant Biotechnology Laboratory of Suntory Ltd., residing at 863-1, Aza-Iketani, Oomori-cho, Youkaiti-shi, Shiga-ken, Japan. The main botanical characteristics of this pollen parent are as follows.

Plant:
*Growth habit*.—Slightly erected spread.
*Plant height*.—5–8 cm.
*Plant extension*.—130–180 cm.
Stem:
*Diameter*.—2.0–3.0 mm.
*Anthocyanin pigmentation*.—Present.
*Branching*.—Medium.
*Pubescence*.—Medium.
*Length of internode*.—4.0–5.0 cm.
Leaf:
*Phyllotaxis*.—Opposite.
*Shape of blade*.—Narrow lanceolate.
*Length*.—3.0–4.0 cm.
*Width*.—2.0–2.5 cm.
*Depth of incision*.—Shallow.
*Color*.—Moderate olive green (R.H.S. 146A, JHS 3509)
*Pubescence*.—Few.
Flower:
*Facing direction*.—Upward.
*Outward curvature of petal*.—Slightly curved.
*Diameter*.—1.7–2.0 cm.
*Height*.—15–20 mm.
*Color*.—Strong purplish pink (R.H.S. 76A, JHS 8904).
*Color intensity*.—Absent.
*Overlapping of petals*.—Separate.
*Spike*.—30–40 mm in length; and 40–50 mm in diameter.
*Calyx*.—1.0 cm in length.
*Anthocyanin pigmentation of calyx limb*.—Present.
*Penducle*.—1–2 mm in thickness; and 5.0 cm in length.
*Number of flowers*.—Plentiful (13–15).
*Reproductive organs*.—1 pistil and 5 stamens.
*Flower fragrance*.—Absent.
*Flowering duration*.—Short.
Physiological and ecological characteristics: High resistance to diseases and pests, high tolerances to heat and moderate tolerances to cold.

This new variety of verbena plant "Sunvp-Pi" was asexually reproduced by cutting at the aforementioned Plant Biotechnology Laboratory of Suntory Ltd., residing at 863-1 Aza-Iketani, Oomori-cho, Youkaiti-shi, Shiga-ken, Japan, and the homogeneity and stability thereof were confirmed.

SUMMARY OF THE VARIETY

This new variety of verbena plant has spread growth habit having long stems and spreading area of plant of broad. The plant has abundant branching and plentiful number of flower in a spike, and great profusion of blooms. The Blooming periods is late April to November and flowering duration is long. And whole bush remains in bloom for a considerable period of time. The flower size is large and the petal color of flower is deep purplish pink color. The plant is highly tolerant to cold and heat, and high in resistance to pests and diseases, particularly powdery mildew.

DESCRIPTION OF THE VARIETY

Figure 1:
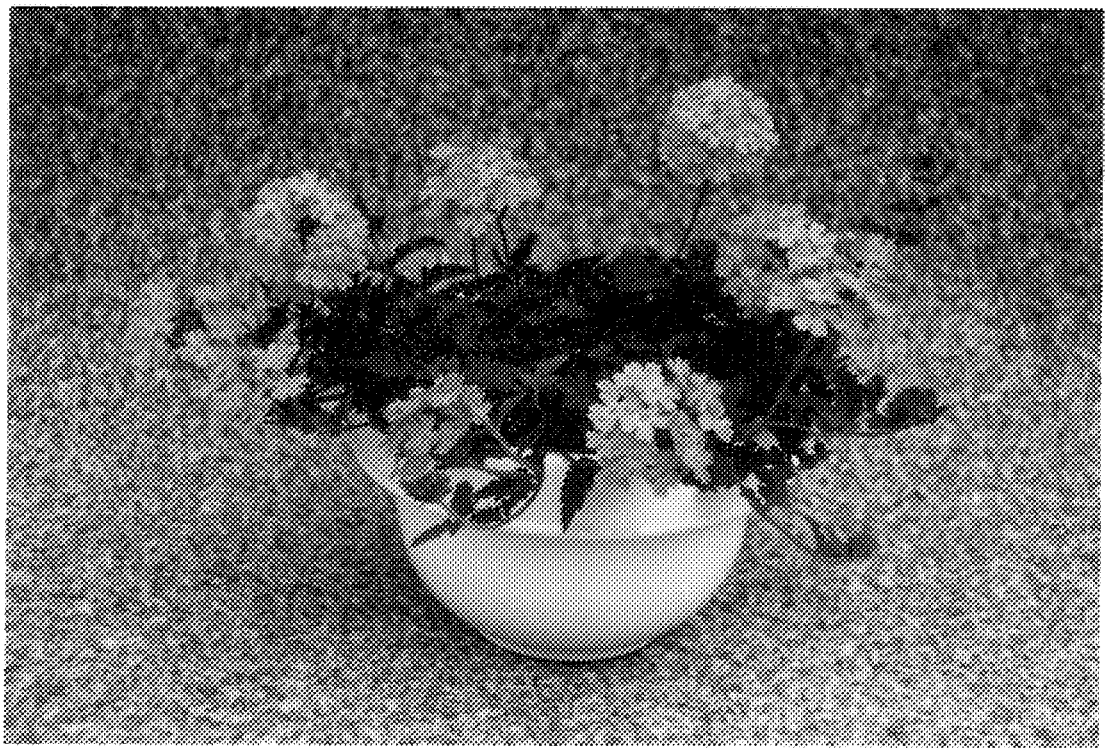
FIG. 1 is a photograph giving a partial view of the new variety of verbena plant planted in a flower pot.
Figure 2:
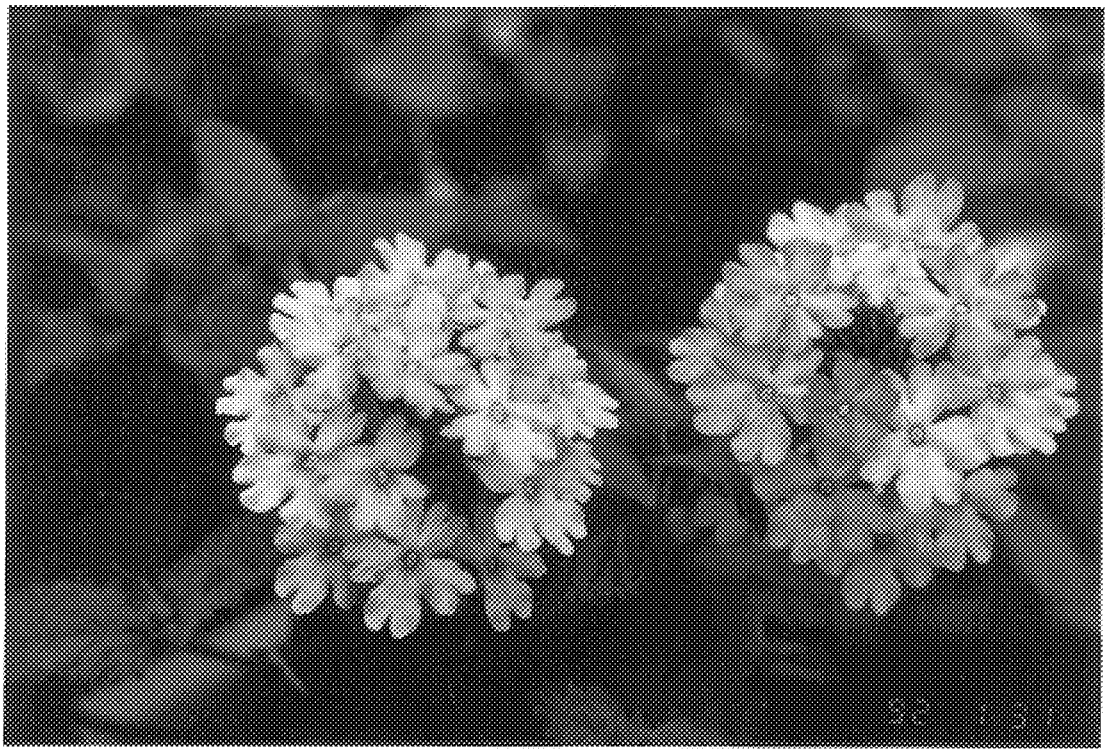
FIG. 2 is a photograph of flowers of the new variety of verbena plant.

The botanical characteristics of the new and distinct variety of verbena plant, "Sunvp-Pi" are as follows.

Plant:
*Growth habit*.—Spread.
*Plant height*.—15–25 cm.
*Plant extension*.—50–70 cm.
*Plant extension*.—50–70 cm.
*Growth*.—Very vigorous with abundant branching and great profusion of blooms; the whole bush remaining in bloom for a considerable period of time.
Stem:
*Diameter*.—2.0–3.0 mm.
*Anthocyanin pigmentation*.—Present.
*Branching*.—Abundant.
*Pubescence*.—Medium.
*Length of internode*.—4.0–5.0 cm.
Leaf:
*Phyllotaxis*.—Opposite.
*Shape of blade*.—Hastate.
*Length*.—4.0–5.0 cm.
*Width*.—2.0–2.5 cm.
*Depth of incision*.—Shallow.
*Color*.—Grayish olive green (R.H.S. 137A–137B, JHS 3716)
*Pubescence*.—Few.
Flower:
*Facing direction*.—Upward.
*Outward curvature of petal*.—Curved.
*Diameter*.—1.5–2.0 cm.
*Height*.—20 mm.
*Color*.—Deep purplish pink (R.H.S. 70C, JHS 9213).
*Color intensity*.—Present.
*Overlapping of petals*.—Separate.
*Spike*.—30–35 mm in length; and 50–55 mm in diameter.
*Calyx*.—1.0 cm in length.
*Anthocyanin pigmentation of calyx limb*.—Present.
*Peduncle*—2–3 mm in thickness; and 5.0–6.0 cm in length.
*Number of flowers*.—Plentiful (13–15).
*Reproductive organs*.—1 pistil and 5 stamens.
*Flower fragrance*.—Absent.
*Flowering duration*.—Long.
Physiological and ecological characteristics: High resistance to diseases and pests, particularly powdery mildew. High tolerance to heat and moderate tolerances to cold.

This new variety of verbena plant is most suitable for flower bedding and potting, particularly in planters, and is further excellent for ground cover.

The plant of this new variety, "Sunvp-Pi" is presently planted and maintained at the Plant Biotechnology Laboratory of Suntory Ltd., residing at 863-1 Aza-Iketani, Oomori-cho, Youkaiti-shi, Shiga-gun, Japan.

I claim:

1. A new and distinct variety of verbena plant, substantially as herein illustrated and described, characterized particularly as to novelty by (A) being a spread growth habit having long stems, (B) an abundant branching and plentiful number of flowers in a spike and great profusion blooms, the whole bush remaining in bloom for a considerable period of time, (C) flower size is large and the petal color of flower is deep purplish pink color, (D) a high resistance to rain, heat, drought, cold and pests.

* * * * *